(12) United States Patent
Fujioka et al.

(10) Patent No.: US 7,498,031 B2
(45) Date of Patent: Mar. 3, 2009

(54) THERAPEUTIC AGENTS FOR INNER EAR DISORDERS CONTAINING AN IL-6 ANTAGONIST AS AN ACTIVE INGREDIENT

(75) Inventors: Masato Fujioka, Tokyo (JP); Hirotaka James Okano, Tokyo (JP); Kaoru Ogawa, Tokyo (JP); Hideyuki Okano, Tokyo (JP); Sho Kanzaki, Tokyo (JP)

(73) Assignees: Chugai Seiyaku Kabushiki Kaisha, Tokyo (JP); Keio University, Tokyo (JP)

( * ) Notice: Subject to any disclaimer, the term of this patent is extended or adjusted under 35 U.S.C. 154(b) by 0 days.

(21) Appl. No.: 10/593,776

(22) PCT Filed: Mar. 24, 2005

(86) PCT No.: PCT/JP2005/006202
§ 371 (c)(1),
(2), (4) Date: Sep. 22, 2006

(87) PCT Pub. No.: WO2005/089802
PCT Pub. Date: Sep. 29, 2005

(65) Prior Publication Data
US 2007/0207153 A1    Sep. 6, 2007

(30) Foreign Application Priority Data
Mar. 24, 2004    (JP) ............................ 2004-087270
Sep. 15, 2004    (JP) ............................ 2004-268800

(51) Int. Cl.
*A61K 39/395*    (2006.01)

(52) U.S. Cl. ............... 424/144.1; 424/143.1; 424/133.1
(58) Field of Classification Search ....................... None
See application file for complete search history.

(56) References Cited

U.S. PATENT DOCUMENTS

| 5,530,101 | A  | * | 6/1996 | Queen et al. ............. 530/387.3 |
| 5,888,510 | A  | * | 3/1999 | Kishimoto et al. ....... 424/141.1 |
| 6,723,319 | B1 | * | 4/2004 | Ito et al. .................. 424/143.1 |
| 2001/0004456 | A1 | | 6/2001 | Tobinick |

FOREIGN PATENT DOCUMENTS

| EP | 0 603 393 A1 | 6/1994 |
| EP | 0 783 893 A1 | 7/1997 |
| EP | 0 791 359 A1 | 8/1997 |
| EP | 0 811 384 A1 | 12/1997 |
| EP | 0 983 767 A1 | 3/2000 |
| EP | 1 004 315 A1 | 5/2000 |

(Continued)

OTHER PUBLICATIONS

Chuntharapai et al (1997) Methods in Enzymology, vol. 288, pp. 15-27.*

(Continued)

*Primary Examiner*—Prema Mertz
(74) *Attorney, Agent, or Firm*—Foley & Lardner LLP

(57) ABSTRACT

A therapeutic and/or preventive agent for inner ear disorders comprising an IL-6 antagonist, preferably an anti-IL-6R antibody, as an active ingredient.

9 Claims, 7 Drawing Sheets

FOREIGN PATENT DOCUMENTS

| | | |
|---|---|---|
| EP | 1 074 268 A1 | 2/2001 |
| EP | 1074268 * | 2/2001 |
| EP | 1 108 435 A1 | 6/2001 |
| EP | 1 334 731 A1 | 8/2003 |
| EP | 1 374 900 A1 | 1/2004 |
| WO | WO 92/19759 | 11/1992 |

OTHER PUBLICATIONS

Hirata, Yuuichi et al., "Characterization of IL-6 Receptor Expression by Monoclonal and Polyclonal Antibodies", The Journal of Immunology, 1989, vol. 143, No. 9, pp. 2900-2906.

Matsuda, Tadashi et al., "Establishment of an interlukin 6 (IL 6)/B Cell Stimulatory Factor 2-dependent Cell Line and Preparation of Anti-IL6 Monoclonal Antibodies", Eur. J. Immunology, 1988, vol. 18, No. 6, pp. 951-956.

Satoh, Hitoshi et al., "Tumor Necrosis Factor-α, an Initiator, and Etanercept, an Inhibitor of Cochlear Inflammation", Laryngoscope, 2002, vol. 112, No. 9, pp. 1627-1634.

Tamura, Tatsuya et al., "Soluble Interleukin-6 Receptor Triggers Osteoclast Formation by Interleukin 6", Proc. Natl. Acad. Sci, 1993, vol. 90, pp. 11924-11928.

Lovell, Daniel, (not Carrasco R. et al.) "Biologic Agents for the Treatment of Juvenile Rheumatoid Arthritis," Pediatric Drugs, 2004, 6(3):137-146.

* cited by examiner

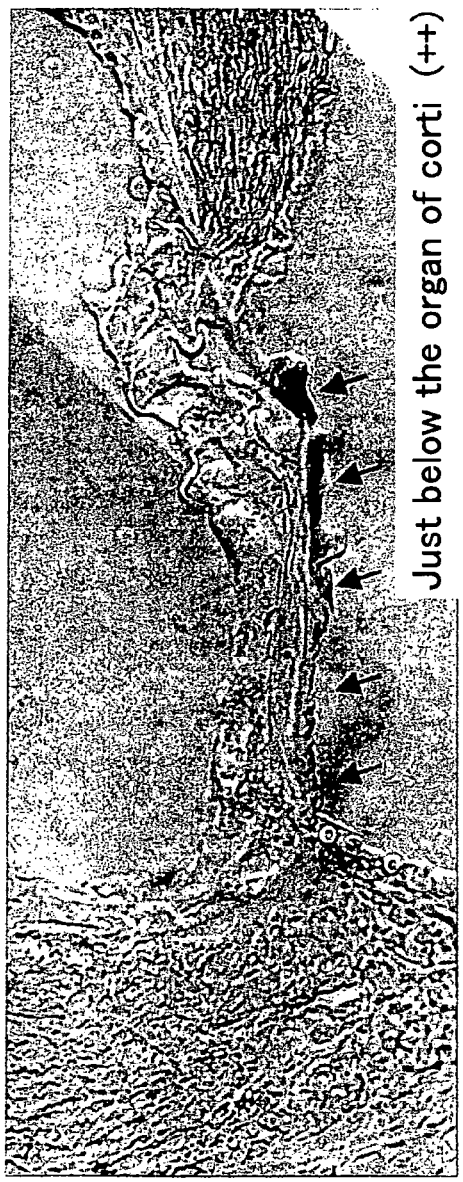 
Fig.6 Just below the organ of corti (++) | Negative control

Spiral ligament (+),
Stria vascularis (−)

THERAPEUTIC AGENTS FOR INNER EAR DISORDERS CONTAINING AN IL-6 ANTAGONIST AS AN ACTIVE INGREDIENT

TECHNICAL FIELD

The present invention relates to a therapeutic and/or preventive agent for inner ear disorders. The preventive and/or therapeutic agent of the present invention comprises an interleukin-6 (IL-6) antagonist.

BACKGROUND ART

Among hearing loss, those that result from labyrinthine (cochlear) or retrocochlear (8th cranial nerve) causes are called sensorineural hearing loss. Causes of sensorineural hearing loss are varied, and include, for example, Meniere's disease, drug-induced inner ear disorders (inner ear disorders due to anti-cancer agents such as aminoglycosides and cisplatin), viral inner ear disorders, purulent inner ear disorders, temporal bone fracture and acoustic nerve tumor. Sudden deafness, senile deafness and noise deafness are also among the sensorineural hearing loss. Noise deafness develops when the inner ear is injured by loud noises from chain saws, internal combustion engines, heavy equipment, guns, airplanes and the like, and is associated with gun firing, snow mobiles, air flight, rock concerts and the like.

Various factors are considered to cause sensorineural hearing loss, in which acute immune reactions responses are known to cause permanent hearing loss (Satoh H. et al., Laryngoscope. 2002 September; 112(9):1627-34). In immune responses in the cochlea caused by the injection of keyhole limpet hemocyanin (KLH) into the inner ear or the subarachnoid, it has been reported, TNF-α and IL-1β have been expressed, TNF-α causes an aggravated disease in the cochlea, and TNF-α inhibitors can partially suppress hearing loss, ibid. However, there are no reports up to now on the contribution of IL-6 to sensorineural hearing loss.

Non-patent document 1:

Satoh H. et al., Laryngoscope. 2002 September; 112(9): 1627-34

DISCLOSURE OF THE INVENTION

The present invention is intended to provide a novel pharmaceutical composition for the treatment and/or prevention of inner ear disorders.

After intensive and extensive research, the present inventors have demonstrated that IL-6 is associated with the pathogenesis of sensorineural hearing loss and that IL-6 antagonists have a therapeutic effect on sensorineural hearing loss.

Thus the present invention provides a therapeutic and/or preventive agent for sensorineural hearing loss, said agent comprising an IL-6 antagonist as an active ingredient.

The above inner ear disorders are for example sensorineural hearing loss which is caused by, for example, Meniere's disease, drug-induced inner ear disorders, viral inner ear disorders, purulent inner ear disorders, temporal bone fracture or acoustic nerve tumor, or they are sudden deafness, senile deafness or noise deafness.

Alternatively, the above inner ear disorders are vestibular disorders, and the vestibular disorders are caused by Meniere's disease, vestibular neuronitis or drug-induced inner ear disorders.

Said IL-6 antagonist is, for example, an antibody against IL-6 receptor. This IL-6 receptor antibody may be, for example, a monoclonal antibody against IL-6 receptor, preferably a monoclonal antibody against human IL-6 receptor or a monoclonal antibody against mouse IL-6 receptor. Said monoclonal antibody against human IL-6 receptor is for example PM-1 antibody, and said monoclonal antibody against mouse IL-6 receptor is for example MR16-1 antibody.

Said antibody against IL-6 receptor is preferably a recombinant antibody. This recombinant antibody is, for example, a chimeric antibody, a humanized antibody, or a human antibody. This humanized antibody is for example a humanized PM-1 antibody.

The present invention may also be described as follows:

[1] The use of an IL-6 antagonist for the manufacture of a therapeutic and/or preventive agent for inner ear disorders.

[2] The use according to [1] wherein said inner ear disorders are sensorineural hearing loss.

[3] The use according to [2] wherein said sensorineural hearing loss is sensorineural hearing loss caused by Meniere's disease, drug-induced inner ear disorders, viral inner ear disorders, purulent inner ear disorders, temporal bone fracture or acoustic nerve tumor.

[4] The use according to [2] wherein said sensorineural hearing loss is sudden deafness, senile deafness or noise deafness.

[5] The use according to [1] wherein said inner ear disorders are vestibular disorders.

[6] The use according to [5] wherein said vestibular disorders are vestibular disorders caused by Meniere's disease, vestibular neuronitis or drug-induced inner ear disorders.

[7] The use according to any of [1] to [6] wherein said IL-6 antagonist is an antibody against IL-6 receptor.

[8] The use according to [7] wherein said antibody against IL-6 receptor is a monoclonal antibody against IL-6 receptor.

[9] The use according to [8] wherein said antibody against IL-6 receptor is a monoclonal antibody against human IL-6 receptor.

[10] The use according to [8] wherein said antibody against IL-6 receptor is a monoclonal antibody against mouse IL-6 receptor.

[11] The use according to any of [7] to [10] wherein said antibody against IL-6 receptor is a recombinant antibody.

[12] The use according to [9] wherein said monoclonal antibody against human IL-6 receptor is PM-1 antibody.

[13] The use according to [10] wherein said monoclonal antibody against mouse IL-6 receptor is MR16-1 antibody.

[14] The use according to any of [7] to [13] wherein said antibody against IL-6 receptor is a chimeric antibody, a humanized antibody, or a human antibody against IL-6 receptor.

[15] The use according to [14] wherein said humanized antibody against IL-6 receptor is a humanized PM-1 antibody.

The present invention may also be described as follows:

[1] A therapeutic and/or preventive method for inner ear disorders which comprises administering an IL-6 antagonist.

[2] The method according to [1] wherein said inner ear disorders are sensorineural hearing loss.

[3] The method according to [2] wherein said sensorineural hearing loss is sensorineural hearing loss caused by Meniere's disease, drug-induced inner ear disorders, viral inner ear disorders, purulent inner ear disorders, temporal bone fracture or acoustic nerve tumor.

[4] The method according to [2] wherein said sensorineural hearing loss is sudden deafness, senile deafness or noise deafness.

[5] The method according to [1] wherein said inner ear disorders are vestibular disorders.

[6] The method according to [5] wherein said vestibular disorders are vestibular disorders caused by Meniere's disease, vestibular neuronitis or drug-induced inner ear disorders.

[7] The method according to any of [1] to [6] wherein said IL-6 antagonist is an antibody against IL-6 receptor.

[8] The method according to [7] wherein said antibody against IL-6 receptor is a monoclonal antibody against IL-6 receptor.

[9] The method according to [8] wherein said antibody against IL-6 receptor is a monoclonal antibody against human IL-6 receptor.

[10] The method according to [8] wherein said antibody against IL-6 receptor is a monoclonal antibody against mouse IL-6 receptor.

[11] The method according to any of [7] to [10] wherein said antibody against IL-6 receptor is a recombinant antibody.

[12] The method according to [9] wherein said monoclonal antibody against human IL-6 receptor is PM-1 antibody.

[13] The method according to [10] wherein said monoclonal antibody against mouse IL-6 receptor is MR16-1 antibody.

[14] The method according to any of [7] to [13] wherein said antibody against IL-6 receptor is a chimeric antibody, a humanized antibody, or a human antibody against IL-6 receptor.

[15] The method according to [14] wherein said humanized antibody against IL-6 receptor is a humanized PM-1 antibody.

BRIEF EXPLANATION OF THE DRAWINGS

FIG. 6 is a photograph substituted for drawings showing the result in which IL-6 was detected with anti-mouse IL-6 antibody using Vectastein ABC kit in the tissue of SD rats six hours after they were subjected to acoustic load in Example 2.

BEST MODE FOR CARRYING OUT THE INVENTION

Figure 1:
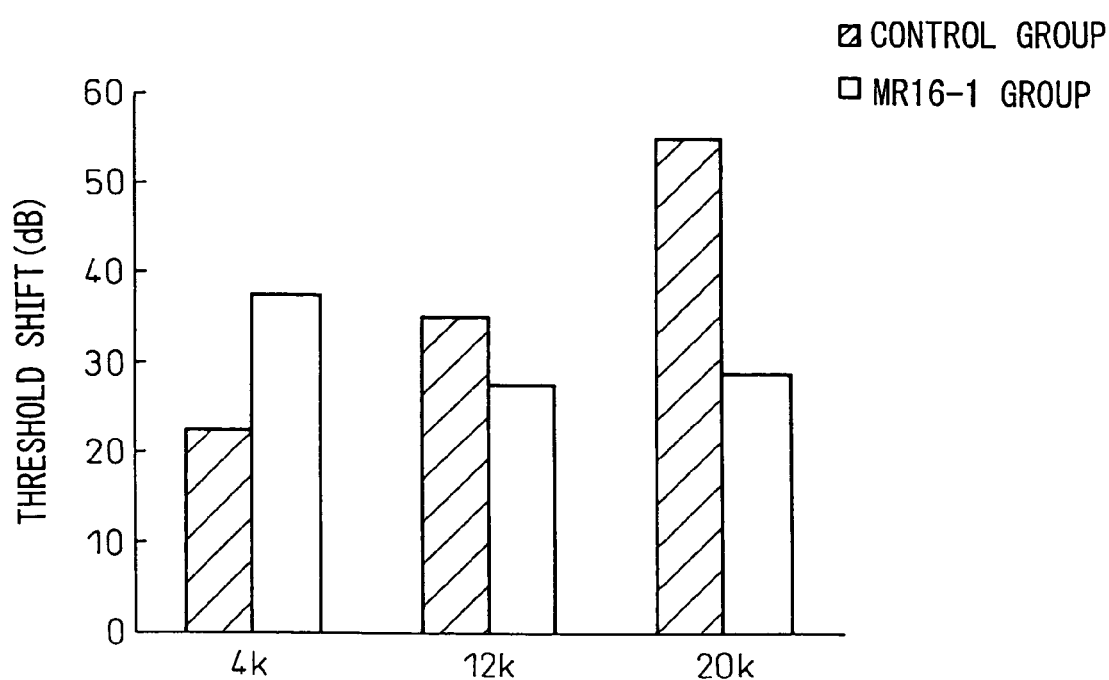
FIG. 1 shows the result of Example 1, and is a graph showing the degree of reduction of hearing threshold level (dB) for the group that received an anti-IL-6R humanized antibody (MR16-1) of the present invention and the control group that received the mouse immunoglobulin G in the mouse model of hearing loss created using three types of frequencies.

The therapeutic agent of the present invention has an effect of suppressing the progression of hearing ability reduction in the tissue damage of the cochlea, i.e. sensorineural hearing loss in the inner ear. Specifically, the therapeutic agent of the present invention has an effect of suppressing hearing ability reduction in the high frequency region in sensorineural hearing loss. As diseases in which damaged hair cells are involved, as in sensorineural hearing loss, there can be mentioned vestibular disorders. In sensorineural hearing loss, the cochlea has been damaged, and the cochlea and the vestibule are responsible for different sensations, but their structures are similar in that hair cells and supporting cells have been covered by the lymph, and their similar tissue constitution and physical properties are responsible for physiological functions. Thus, it has been designed such that a similar mechanism detects different sensations based on the difference whether the hair cells detected sound vibrations or they detected lymph movement by acceleration. Damage to either of the cochlea and the vestibule lead to the reduced function, and sensitivity to drugs is extremely similar. Thus, the therapeutic agent of the present invention is effective for the treatment of inner ear disorders such as sensorineural hearing loss and vestibular disorders.

IL-6 is a cytokine which is also called B cell stimulating factor 2 (BSF2) or interferon β2. IL-6 was discovered as a differentiation factor involved in the activation of B-lymphatic cells (Hirano, T. et al., Nature (1986) 324, 73-76). Thereafter, it was found to be a multifunctional cytokine that influences various functions of the cell (Akira, S. et al., Adv. in Immunology (1993) 54, 1-78). IL-6 has been reported to induce the maturation of T-lymphatic cells (Lotz, M. et al., J. Exp. Med. (1988) 167, 1253-1258).

IL-6 transmits its biological activity through two types of proteins on the cell. One of them is IL-6 receptor, a ligand-biding protein with a molecular weight of about 80 kD, to which IL-6 binds (Taga, T. et al., J. Exp. Med. (1987) 166, 967-981; Yamasaki, K. et al., Science (1987) 241, 825-828). IL-6 receptor occurs not only in the membrane-bound form that penetrates through and is expressed on the cell membrane but also as a soluble IL-6 receptor consisting mainly of the extracellular region.

The other is a membrane-bound protein gp130 having a molecular weight of about 130 kD that is involved in non-ligand-binding signal transduction. IL-6 and IL-6 receptor form the IL-6/IL-6 receptor complex which, after binding to gp130, transmits its biological activity to the cell (Taga, T. et al., Cell (1989) 58, 573-581).

An IL-6 antagonist is a substance that inhibits the transduction of biological activity of IL-6. There have been known so far antibody directed against IL-6 (anti-IL-6 antibody), antibody directed against IL-6 receptor (anti-IL-6 receptor antibody), antibody directed against gp130 (anti-gp130 antibody), altered IL-6, partial peptides of IL-6 or IL-6 receptor and the like.

Anti-IL-6 receptor antibody has been described in several reports (Novick D. et al., Hybridoma (1991) 10, 137-146, Huang, Y. W. et al., Hybridoma (1993) 12, 621-630, International Patent Publication WO 95-09873, French Patent Application FR 2694767, U.S. Pat. No. 5,216,28). Humanized PM-1 antibody has been known that was obtained by transplanting the complementarity determining region (CDR) of one of them, a mouse antibody PM-1 (Hirata, Y. et al., J. Immunology (1989) 143, 2900-2906), to a human antibody (the International Patent Publication WO 92-19759).

The above IL-6 antagonist is preferably an antibody against IL-6 receptor, preferably a monoclonal antibody against human IL-6 receptor or a monoclonal antibody against mouse IL-6 receptor. As the above monoclonal antibody against human IL-6 receptor, there can be illustrated PM-1 antibody, and as the above monoclonal antibody against mouse IL-6 receptor, there can be illustrated MR16-1 antibody. The above antibody is preferably a chimeric antibody, a humanized antibody or a human antibody, for example a humanized PM-1 antibody. A humanized antibody is an altered antibody also referred to as a reshaped human antibody.

IL-6 antagonists for use in the present invention may be of any origin, any kind, and any form, as long as they are useful for the treatment and/or prevention of inner ear disorders.

IL-6 antagonists block signal transduction by IL-6 and inhibit the biological activity of IL-6. IL-6 antagonists are preferably substances that have an activity of inhibiting the binding to any of IL-6, IL-6 receptor, and gp130. As the IL-6 antagonists, there can be mentioned for example anti-IL-6 antibody, anti-IL-6 receptor antibody, anti-gp130 antibody, altered IL-6, altered soluble IL-6 receptor, a partial peptide of IL-6 or IL-6 receptor, and a low molecular weight substance having the same activity as these.

Anti-IL-6 antibodies for use in the present invention can be obtained as polyclonal or monoclonal antibodies using a known method. As the anti-IL-6 antibodies for use in the present invention, monoclonal antibodies of, in particular, a mammalian origin, are preferred. Monoclonal antibodies of a mammalian origin include those produced by a hybridoma and recombinant antibody produced by a host which has been transformed with an expression vector containing genetically engineered antibody genes. These antibodies, via binding to IL-6, block the binding of IL-6 to IL-6 receptor and, thereby, block the signal transduction of biological activity of IL-6 into the cell.

Examples of such antibodies include MH166 (Matsuda T. et al., Eur. J. Immunol. (1988) 18, 951-956) and SK2 antibody (Sato, K. et al., The 21st Nihon Menekigakkai Soukai (General Meeting of the Japan Immunology Society), Academic Record (1991) 21, 166) and the like.

An anti-IL-6 antibody-producing hybridoma can be basically constructed using a known procedure as described below. Thus, IL-6 may be used as a sensitizing antigen and is immunized in the conventional method of immunization. The immune cells thus obtained are fused with known parent cells in the conventional cell fusion process, and then monoclonal antibody-producing cells are screened by the conventional screening method to prepare the desired hybridoma.

Specifically, anti-IL-6 antibody may be obtained in the following manner. For example, a human IL-6 for use as the sensitizing antigen to obtain antibody can be obtained using the IL-6 gene/amino acid sequence disclosed in Eur. J. Biochem (1987) 168, 543-550, J. Immunol. (1988) 140, 1534-1541, or Argic. Biol. Chem. (1990) 54, 2685-2688.

After a suitable host cell is transformed by inserting the IL-6 gene sequence into a known expression vector system, the IL-6 protein of interest is purified from the host cell or the culture supernatant thereof, and the purified IL-6 protein can be used as the sensitizing antigen. Alternatively, a fusion protein of the IL-6 protein and another protein may be used as the sensitizing antigen.

Anti-IL-6 receptor antibodies for use in the present invention can be obtained as polyclonal or monoclonal antibodies using a known method. As the anti-IL-6 receptor antibodies for use in the present invention, monoclonal antibodies of, in particular, mammalian origin are preferred. Monoclonal antibodies of a mammalian origin include those produced by a hybridoma and those produced by a host which has been transformed with an expression vector containing genetically engineered antibody genes. The antibodies, via binding to IL-6 receptor, inhibit the binding of IL-6 to IL-6 receptor, and thereby block the transduction of the biological activity of IL-6 into the cell.

Examples of such antibodies include MR16-1 antibody (Tamura, T., et al., Proc. Natl. Acad. Sci. USA (1993) 90, 11924-11928), PM-1 antibody (Hirata, Y. et al., J. Immunol. (1989) 143, 2900-2906), or AUK12-20 antibody, AUK64-7 antibody or AUK146-15 antibody (International Patent Publication WO 92-19759) and the like. Among them, PM-1 antibody is most preferred.

Incidentally, the hybridoma cell line which produces PM-1 antibody has been internationally deposited under the provisions of the Budapest Treaty as PM-1 on Jul. 12, 1989 with the Patent Microorganism Depository of National Institute of Industrial Science and Technology at Chuo 6, 1-1, Higashi 1-chome, Tsukuba city, Ibaraki pref., Japan, as FERM BP-2998. The hybridoma cell line which produces MR16-1 antibody has been internationally deposited under the provisions of the Budapest Treaty as MR16-1 on Mar. 13, 1997 with the Patent Microorganism Depository of National Institute of Industrial Science and Technology at Chuo 6, 1-1, Higashi 1-chome, Tsukuba city, Ibaraki pref., Japan, as FERM BP-5875.

Hybridomas producing anti-IL-6 receptor monoclonal antibody can be basically prepared using a known procedure as described bellow. Thus, IL-6 receptor is used as a sensitizing antigen and is immunized according to the conventional method of immunization. The immune cells thus obtained are fused with known parent cells in the conventional cell fusion process, and then monoclonal antibody-producing cells may be screened by the conventional screening method to prepare the desired hybridoma.

Specifically, anti-IL-6 receptor antibody may be prepared in the following manner. For example, the human IL-6 receptor used as the sensitizing antigen for obtaining antibody can be obtained using the IL-6 receptor gene sequence/amino acid sequence disclosed in European Patent Application EP 325474, and the mouse IL-6 receptor can be obtained using the IL-6 receptor gene disclosed in Japanese Unexamined Patent Publication (Kokai) 3-155795.

There are two types of IL-6 receptor proteins: IL-6 receptor expressed on the cell membrane, and IL-6 receptor detached from the cell membrane (soluble IL-6 receptor) (Yasukawa K. et al., J. Biochem. (1990) 108, 673-676). Soluble IL-6 receptor antibody is composed substantially of the extracellular region of the IL-6 receptor bound to the cell membrane, and thereby is different from the membrane-bound IL-6 receptor in that the former lacks the transmembrane region or both of the transmembrane region and the intracellular region. As the IL-6 receptor protein, any IL-6 receptor can be used, as long as it can be used a sensitizing antigen for production of the anti-IL-6 receptor antibody for use in the present invention.

After the gene sequence of IL-6 receptor is inserted into a known expression vector system to transform an appropriate host cell, the desired IL-6 receptor protein may be purified from the host cell or a culture supernatant thereof using a known method, and the purified IL-6 receptor protein may be used as the sensitizing antigen. Alternatively, cells that are expressing IL-6 receptor or a fusion protein of the IL-6 receptor protein and another protein may be used as the sensitizing antigen.

*Escherichia coli* (*E. coli*) that has a plasmid pIBIBSF2R containing cDNA encoding human IL-6 receptor has been internationally deposited under the provisions of the Budapest Treaty as HB101-pIBIBSF2R on Jan. 9, 1989 with the Patent Microorganism Depository of National Institute of Industrial Science and Technology at Chuo 6, 1-1, Higashi 1-chome, Tsukuba city, Ibaraki pref., Japan, as FERM BP-2232.

Anti-gp130 antibodies for use in the present invention can be obtained as polyclonal or monoclonal antibodies using a known method. As the anti-gp130 antibodies for use in the present invention, monoclonal antibodies of, in particular, mammalian origin are preferred. Monoclonal antibodies of a mammalian origin include those produced by a hybridoma and those produced by a host which has been transformed with an expression vector containing genetically engineered antibody genes. The antibodies, via binding to gp130, inhibit the binding of IL-6/IL-6 receptor complex to gp130, and thereby block the transduction of the biological activity of IL-6 into the cell.

Examples of such antibodies include AM64 antibody (Japanese Unexamined Patent Publication (Kokai) 3-219894), 4B11 antibody and 2H4 antibody (U.S. Pat. No. 5,571,513), B-S12 antibody and B-P8 antibody (Japanese Unexamined Patent Publication (Kokai) 8-291199) and the like.

An anti-gp130 monoclonal antibody-producing hybridoma can be basically created using a known procedure as described below. Thus, gp130 may be used as a sensitizing antigen and is immunized in the conventional method of immunization. The immune cells thus obtained are fused with known parent cells in the conventional cell fusion process, and then the monoclonal antibody-producing hybridomas are screened by the conventional screening method to prepare the desired hybridoma.

Specifically, monoclonal antibody may be obtained in the following manner. For example, gp130 used as the sensitizing antigen for antibody generation can be obtained using the gp130 gene sequence/amino acid sequence disclosed in European Patent Application EP 411946.

After a suitable host cell is transformed by inserting the gp130 gene sequence into a known expression vector system, the gp130 protein of interest is purified from the host cell or from the culture supernatant thereof in a conventional method. The purified gp130 receptor protein can be used as the sensitizing antigen. Alternatively, a fusion protein of the gp130 protein and another protein may be used as the sensitizing antigen.

Though mammals to be immunized with the sensitizing antigen are not specifically limited, they are preferably selected in consideration of their compatibility with the parent cell for use in cell fusion. They generally include rodents such as mice, rats, hamsters and the like.

Immunization of animals with a sensitizing antigen is carried out using a known method. A general method, for example, involves the intraperitoneal or subcutaneous injection of a sensitizing antigen to the mammal. Specifically, a sensitizing antigen which has been diluted and suspended in an appropriate amount of phosphate buffered saline (PBS) or physiological saline etc. is mixed, as desired, with an appropriate amount of a common adjuvant, for example Freund's complete adjuvant. After being emulsified, it is preferably administered to a mammal several times every 4 to 21 days. Alternatively a suitable carrier may be used at the time of immunization of the sensitizing antigen.

After immunization and the confirmation of the increase in the desired antibody levels in the serum, the immune cells are taken out from the mammal and are subjected to cell fusion. Preferred immune cells to be subjected to cell fusion include, in particular, spleen cells.

The mammalian myeloma cells as the other parent cells which are fused with the above-mentioned immune cells preferably include various known cell lines such as P3X63Ag8.653 (Kearney, J. F. et al., J. Immunol. (1979) 123, 1548-1550), P3X63Ag8U.1 (Current Topics in Microbiology and Immunology (1978) 81, 1-7), NS-1 (Kohler, G. and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. F. et al., J. Immunol. Methods (1980) 35; 1-21), S194 (Trowbridge, I. S., J. Exp. Med. (1978) 148, 313-323), R210 (Galfre, G. et al., Nature (1979) 277; 131-133) and the like.

Cell fusion between the above immune cells and the myeloma cells may be essentially conducted in accordance with a known method such as that described in Milstein et al. (Kohler, G. and Milstein, C., Methods Enzymol. (1981) 73, 3-46) and the like.

More specifically, the above cell fusion is carried out in the conventional nutrient broth in the presence of, for example, a cell fusion accelerator. As the cell fusion accelerator, for example, polyethylene glycol (PEG), Sendai virus (HVJ) and the like may be used, and, in addition, an adjuvant such as dimethyl sulfoxide etc. may be added as desired to enhance the efficiency of fusion.

The preferred ratio of the immune cells and the myeloma cells to be used is, for example, 1 to 10 times more immune cells than the myeloma cells. Examples of culture media to be used for the above cell fusion include RPMI1640 medium and MEM culture medium suitable for the growth of the above myeloma cell lines, and the conventional culture medium used for this type of cell culture and, besides, a serum supplement such as fetal calf serum (FCS) may be added.

In cell fusion, predetermined amounts of the above immune cells and the myeloma cells are mixed well in the above culture liquid, to which a PEG solution previously heated to about 37° C., for example a PEG solution with a mean molecular weight of about 1000 to 6000, is added at a concentration of 30 to 60% (w/v) and mixed to form the desired fusion cells (hybridoma). Then, by repeating the sequential addition of a suitable culture liquid and centrifugation to remove the supernatant, cell fusion agents etc. which are undesirable for the growth of the hybridoma can be removed.

Said hybridoma may be selected by culturing in the conventional selection medium, for example, the HAT culture medium (a culture liquid containing hypoxanthine, aminopterin, and thymidine). Culturing in said HAT culture liquid is continued generally for a period of time sufficient to effect killing of the cells (non-fusion cells) other than the desired hybridoma, generally several days to several weeks. Then the conventional limiting dilution method is conducted to effect the screening and cloning of the hybridomas that produce the desired antibody.

In addition to obtaining the above hybridoma by immunizing an animal other than the human with an antigen, it is also possible to sensitize human lymphocytes in vitro with a desired antigen protein or desired antigen-expressing cells, and the resulting sensitized B lymphocytes are fused with human myeloma cells, for example U266, to obtain the desired human antibody having the activity of binding to the desired antigen or the desired antigen-expressing cells (see Japanese Post-examined Patent Publication (Kokoku) No. 1-59878). Furthermore, a transgenic animal having a repertoire of all human antibody genes is immunized with the antigen or the antigen-expressing cells to obtain the desired human antibody in the method described above (see International Patent Publication WO 93/12227, WO 92/03918, WO 94/02602, WO 94/25585, WO 96/34096 and WO 96/33735).

The monoclonal antibody-producing hybridoma thus constructed can be subcultured in the conventional culture liquid, or can be stored for a prolonged period of time in liquid nitrogen.

In order to obtain monoclonal antibodies from said hybridoma, a method can be used in which said hybridoma is cultured in the conventional method and the antibodies are obtained as the supernatant, or a method in which the hybridoma is administered to and grown in a mammal compatible with said hybridoma and the antibodies are obtained as the ascites. The former method is suitable for obtaining high-purity antibodies, whereas the latter is suitable for a large scale production of antibodies.

For example, a hybridoma producing anti-IL-6 receptor antibody can be constructed using the method disclosed in Japanese Unexamined Patent Publication (Kokai) 3-139293. It can be conducted by a method in which the PM-1 antibody-producing hybridoma that was internationally deposited under the provisions of the Budapest Treaty as FERM BP-2998 on Jul. 12, 1989 with the Patent Microorganism Depository of National Institute of Industrial Science and Technology, of Chuo 6, 1-1, Higashi 1-chome, Tsukuba city, Ibaraki pref., Japan, is intraperitoneally injected to BALB/c mice to obtain the ascites from which the PM-1 antibody is purified, or a method in which said hybridoma is cultured in a suitable culture medium such as the RPMI1640 medium containing 10% bovine fetal serum and 5% BM-Condimed Hi (manufactured by Boehringer Mannheim), the hybridoma SFM medium (manufactured by GIBCO-BRL), the PFHM-II medium (manufactured by GIBCO-BRL) and the like, and the PM-1 antibody can be purified from the supernatant.

A recombinant antibody which was produced by the recombinant gene technology in which an antibody gene was cloned from the hybridoma and integrated into a suitable vector which was then introduced into a host can be used in the present invention as monoclonal antibody (see, for example, Borrebaeck C. A. K., and Larrick J. W. THERAPEUTIC MONOCLONAL ANTIBODIES, published in the United Kingdom by MACMILLAN PUBLISHERS LTD. 1990).

Specifically, mRNA encoding the variable (V) region of the desired antibody is isolated from antibody-producing cells such as a hybridoma. The isolation of mRNA is conducted by preparing total RNA using, for example, a known method such as the guanidine ultracentrifuge method (Chirgwin, J. M. et al., Biochemistry (1979) 18, 5294-5299), the AGPC method (Chomczynski, P. et al., Anal. Biochem. (1987) 162, 156-159), and then mRNA is prepared from the total RNA using the mRNA Purification kit (manufactured by Pharmacia) and the like. Alternatively, mRNA can be directly prepared using the QuickPrep mRNA Purification Kit (manufactured by Pharmacia).

cDNA of the V region of antibody may be synthesized from the mRNA thus obtained using a reverse transcriptase. cDNA may be synthesized using the AMV Reverse Transcriptase First-strand cDNA Synthesis Kit and the like. Alternatively, for the synthesis and amplification of cDNA, the 5'-Ampli FINDER RACE Kit (manufactured by Clontech) and the 5'-RACE method (Frohman, M. A. et al., Proc. Natl. Acad. Sci. USA (1988) 85, 8998-9002; Belyavsky, A. et al., Nucleic Acids Res. (1989) 17, 2919-2932) that employs polymerase chain reaction (PCR) may be used. The desired DNA fragment is purified from the PCR product obtained and may be ligated to vector DNA. Moreover, a recombinant vector is constructed therefrom and then is introduced into E. coli etc., from which colonies are selected to prepare the desired recombinant vector. The base sequence of the desired DNA may be confirmed by a known method such as the dideoxy method.

Once the DNA encoding the V region of the desired antibody has been obtained, it may be ligated to DNA encoding the constant region (C region) of the desired antibody, which is then integrated into an expression vector. Alternatively, the DNA encoding the V region of the antibody may be integrated into an expression vector containing DNA encoding the C region of the antibody.

In order to produce the antibody for use in the present invention, the antibody gene is integrated as described below into an expression vector so as to be expressed under the control of the expression regulatory region, for example an enhancer and/or a promoter. Subsequently, the expression vector may be transformed into a host cell and the antibody can then be expressed therein.

In accordance with the present invention, artificially altered recombinant antibody such as chimeric antibody, humanized antibody, and human antibody can be used for the purpose of lowering heterologous antigenicity against humans. These altered antibodies can be produced using known methods.

Chimeric antibody can be obtained by ligating the thus obtained DNA encoding the V region of antibody to DNA encoding the C region of human antibody, which is then integrated into an expression vector and introduced into a host for production of the antibody therein (see European Patent Application EP 125023, and International Patent Publication WO 92-19759). Using this known method, chimeric antibody useful for the present invention can be obtained.

For example, a plasmid that contains DNA encoding the L chain V region or the H chain V region of chimeric PM-1 antibody was designated as pPM-k3 or pPM-h1, respectively, and E. coli having the plasmid has been internationally deposited under the provisions of the Budapest Treaty as NCIMB 40366 and NCIMB 40362, respectively, on Feb. 12, 1991 with the National Collections of Industrial and Marine Bacteria Limited.

Humanized antibody which is also called reshaped human antibody has been made by transplanting the complementarity determining region (CDR) of antibody of a mammal other than the human, for example mouse antibody, into the complementarity determining region of human antibody. The general recombinant DNA technology for preparation of such antibodies is also known (see European Patent Application EP 125023 and International Patent Publication WO 92-19759).

Specifically, a DNA sequence which was designed to ligate the CDR of mouse antibody with the framework region (FR) of human antibody is synthesized from several divided oligonucleotides having sections overlapping with one another at the ends thereof by the PCR method. The DNA thus obtained is ligated to the DNA encoding the C region of human antibody and then is integrated into an expression vector, which is introduced into a host for antibody production (see European Patent Application EP 239400 and International Patent Publication WO 92-19759).

For the FR of human antibody ligated through CDR, those in which the complementarity determining region that forms a favorable antigen binding site are selected. When desired, amino acids in the framework region of the antibody variable region may be substituted so that the complementarity determining region of reshaped human antibody may form an appropriate antigen biding site (Sato, K. et al., Cancer Res. (1993) 53, 851-856).

For example, for chimeric antibody or humanized antibody, the C region of human antibody is used. As the C region of human antibody, there can be mentioned Cγ, and Cγ1, Cγ2, Cγ3, and Cγ4, for example, can be used. The C region of human antibody may be modified to improve the stability of antibody or the production thereof.

Chimeric antibody consists of the variable region of antibody derived from a mammal other than the human and the C region derived from human antibody, whereas humanized antibody consists of the complementarity determining region of antibody derived from a mammal other than the human and the framework region and the C region derived from human antibody. Accordingly, antigenicity thereof in the human body has been reduced so that they are useful as antibody for use in the present invention.

As a preferred embodiment of the humanized antibody for use in the present invention, there can be mentioned humanized PM-1 antibody (see International Patent Publication WO 92-19759).

Furthermore, as a method of obtaining human antibody, a technology that employs panning with a human antibody library is known, in addition to those described above. For example, the variable region of human antibody is expressed on the surface of a phage by the phage display method as a single chain antibody (scFv) to select a phage that binds to the antigen. By analyzing the gene of the phage selected, the DNA sequence encoding the variable region of the human antibody that binds to the antigen can be determined. Once the DNA sequence of scFv that binds to the antigen is clarified, it is possible to construct an appropriate expression vector that contains said sequence and then to obtain human antibody. These methods are already known and can be found in WO 92/01047, WO 92/20791, WO 93/06213, WO 93/11236, WO 93/19172, WO 95/01438, and WO 95/15388.

Antibody genes constructed as described above may be expressed and obtained in a known method. In the case of mammalian cells, expression may be accomplished using a vector containing a commonly used useful promoter, the antibody gene to be expressed, DNA in which the poly A signal has been operably linked at 3' downstream thereof or a vector containing said DNA. Examples of the promoter/enhancer include human cytomegalovirus immediate early promoter/enhancer.

Additionally, as the promoter/enhancer which can be used for expression of antibody for use in the present invention, there can be used viral promoters/enhancers such as retrovirus, polyoma virus, adenovirus, and simian virus 40 (SV40), and promoters/enhancers derived from mammalian cells such as human elongation factor 1α (HEF1α).

For example, expression may be readily accomplished by the method of Mulligan et al. (Mulligan, R. C. et al., Nature (1979) 277, 108-114) when SV40 promoter/enhancer is used, or by the method of Mizushima et al. (Mizushima, S. and Nagata, S., Nucleic Acids Res. (1990) 18, 5322) when HEF1α promoter/enhancer is used.

In the case of E. coli, expression may be conducted by operably linking a commonly used useful promoter, a signal sequence for antibody secretion, and the antibody gene to be expressed, followed by expression thereof. As the promoter, for example, there can be mentioned lacZ promoter and araB promoter. The method of Ward et al. (Ward, E. S. et al., Nature (1989) 341, 544-546; Ward, E. S. et al., FASEB J. (1992) 6, 2422-2427) may be used when lacz promoter is used, and the method of Better et al. (Better, M. et al., Science (1988) 240, 1041-1043) may be used when araB promoter is used.

As the signal sequence for antibody secretion, when produced in the periplasm of E. coli, the pelB signal sequence (Lei, S. P. et al., J. Bacteriol. (1987) 169, 4379-4383) can be used. After separating the antibody produced in the periplasm, the structure of the antibody is appropriately refolded before use (see, for example, WO 96/30394).

As the origin of replication, there can be used those derived from SV40, polyoma virus, adenovirus, bovine papilloma virus (BPV) and the like. Furthermore, for the amplification of the gene copy number in the host cell system, expression vectors can include as selectable markers the aminoglycoside phosphotransferase (APH) gene, the thymidine kinase (TK) gene, E. coli xanthine guanine phosphoribosyl transferase (Ecogpt) gene, the dihydrofolate reductase (dhfr) gene and the like.

For the production of antibody for use in the present invention, any production system can be used. The production system for antibody preparation comprises the in vitro or the in vivo production system. As the in vitro production system, there can be mentioned a production system which employs eukaryotic cells and the production system which employs prokaryotic cells.

When the eukaryotic cells are used, there are the production systems which employ animal cells, plant cells, or fungal cells. Known animal cells include (1) mammalian cells such as CHO cells, COS cells, myeloma cells, baby hamster kidney (BHK) cells, HeLa cells, and Vero cells, (2) amphibian cells such as *Xenopus oocytes*, or (3) insect cells such as sf9, sf21, and Tn5. Known plant cells include, for example, those derived from *Nicotiana tabacum*, which may be subjected to callus culture. Known fungal cells include yeasts such as the genus *Saccharomyces*, more specifically *Saccharomyces cereviceae*, or filamentous fungi such as the genus *Aspergillus*, more specifically *Aspergillus niger*.

When the prokaryotic cells are used, there are the production systems which employ bacterial cells. Known bacterial cells include *Escherichia coli* (E. coli), and *Bacillus subtilis*.

By introducing via transformation the gene of the desired antibody into these cells and culturing the transformed cells in vitro, the antibody can be obtained. Culturing is conducted in the known methods. For example, as the culture liquid, DMEM, MEM, RPMI1640, and IMDM can be used, and serum supplements such as fetal calf serum (FCS) may be used in combination. In addition, antibodies may be produced in vivo by implanting cells into which the antibody gene has been introduced into the abdominal cavity of an animal and the like.

As in vivo production systems, there can be mentioned those which employ animals and those which employ plants. When animals are used, there are the production systems which employ mammals and insects.

As mammals, goats, pigs, sheep, mice, and cattle can be used (Vicki Glaser, SPECTRUM Biotechnology Applications, 1993). Also as insects, silkworms can be used. When plants are used, tobacco, for example, can be used.

Antibody genes are introduced into these animals or plants, and the antibodies are produced in such animals or plants, and recovered. For example, an antibody gene is inserted into the middle of the gene encoding protein which is inherently produced in the milk such as goat β casein to prepare fusion genes. DNA fragments containing the fusion gene into which the antibody gene has been inserted are injected into a goat embryo, and the embryo is introduced into a female goat. The desired antibody is obtained from the milk produced by the transgenic goat borne to the goat who received the embryo or offsprings thereof. In order to increase the amount of milk containing the desired antibody produced by the transgenic goat, hormones may be given to the transgenic goat as appropriate. (Ebert, K. M. et al., Bio/Technology (1994) 12, 699-702).

When silkworms are used, baculovirus into which the desired antibody gene has been inserted is infected to the silkworm, and the desired antibody can be obtained from the body fluid of the silkworm (Maeda, S. et al., Nature (1985) 315, 592-594). Moreover, when tobacco is used, the desired antibody gene is inserted into an expression vector for plants, for example pMON 530, and then the vector is introduced into a bacterium such as *Agrobacterium tumefaciens*. The bacterium is then infected to tobacco such as *Nicotiana tabacum* to obtain the desired antibody from the leaves of the tobacco (Julian, K. -C. Ma et al., Eur. J. Immunol. (1994) 24, 131-138).

When antibody is produced in vitro or in vivo production systems, as described above, DNA encoding the heavy chain (H chain) or the light chain (L chain) of antibody may be separately integrated into an expression vector and the hosts are transformed simultaneously, or DNA encoding the H chain and the L chain may be integrated into a single expression vector, and the host is transformed therewith (see International Patent Publication WO 94-11523).

Antibodies for use in the present invention may be antibody fragments or modified versions thereof as long as they are preferably used. For example, as fragments of antibody, there may be mentioned Fab, F(ab')$_2$, Fv or single-chain Fv (scFv) in which Fv's of H chain and L chain were ligated via a suitable linker.

Specifically, antibodies are treated with an enzyme, for example, papain or pepsin, to produce antibody fragments, or genes encoding these antibody fragments are constructed, and then introduced into an expression vector, which is expressed in a suitable host cell (see, for example, Co, M. S. et al., J. Immunol. (1994) 152, 2968-2976; Better, M. and Horwitz, A. H., Methods in Enzymology (1989) 178, 476-496; Plueckthun, A. and Skerra, A., Methods in Enzymology (1989) 178, 476-496; Lamoyi, E., Methods in Enzymology (1989) 121, 652-663; Rousseaux, J. et al., Methods in Enzymology (1989) 121, 663-66; Bird, R. E. et al., TIBTECH (1991) 9, 132-137).

scFv can be obtained by ligating the V region of H chain and the V region of L chain of antibody. In scFv, the V region of H chain and the V region of L chain are preferably ligated via a linker, preferably a peptide linker (Huston, J. S. et al., Proc. Natl. Acad. Sci. USA (1988) 85, 5879-5883). The V region of H chain and the V region of L chain in scFv may be derived from any of the above-mentioned antibodies. As the peptide linker for ligating the V regions, any single-chain peptide comprising, for example, 12-19 amino acid residues may be used.

DNA encoding scFv can be obtained using DNA encoding the H chain or the H chain V region of the above antibody and DNA encoding the L chain or the L chain V region of the above antibody as the template by amplifying the portion of the DNA encoding the desired amino acid sequence among the above sequences by the PCR technique with the primer pair specifying the both ends thereof, and by further amplifying the combination of DNA encoding the peptide linker portion and the primer pair which defines that both ends of said DNA be ligated to the H chain and the L chain, respectively.

Once DNAs encoding scFv have been constructed, an expression vector containing them and a host transformed with said expression vector can be obtained by the conventional methods, and scFv can be obtained using the resultant host by the conventional methods.

These antibody fragments can be produced by obtaining the gene thereof in a similar manner to that mentioned above and by allowing it to be expressed in a host. "Antibody" as used herein also encompasses these antibody fragments.

As modified antibodies, antibodies associated with various molecules such as polyethylene glycol (PEG) can be used. "Antibody" as used herein also encompasses these modified antibodies. These modified antibodies can be obtained by chemically modifying the antibodies thus obtained. These methods have already been established in the art.

Antibodies produced and expressed as described above can be separated from the inside or outside of the host cell and then may be purified to homogeneity. Separation and purification of the antibody for use in the present invention may be accomplished by affinity chromatography. As the column used for such affinity chromatography, there can be mentioned Protein A column and Protein G column. Examples of the carriers used in the Protein A column are Hyper D, POROS, Sepharose F. F. and the like. Alternatively, methods for separation and purification conventionally used for proteins can be used without any limitation.

Separation and purification of the antibody for use in the present invention may be accomplished by combining, as appropriate, chromatography other than the above-mentioned affinity chromatography, filtration, ultrafiltration, salting-out, dialysis and the like. Chromatography includes, for example, ion exchange chromatography, hydrophobic chromatography, gel-filtration and the like. These chromatographies can be applied into high performance liquid chromatography (HPLC). Alternatively, reverse-phase HPLC can be used.

The concentration of antibody obtained in the above can be determined by the measurement of absorbance or by ELISA and the like. Thus, when absorbance measurement is employed, a sample is appropriately diluted with PBS(−) and then the absorbance is measured at 280 nm, followed by calculation using the absorption coefficient of 1.35 OD at 1 mg/ml. When the ELISA method is used, measurement is conducted as follows. Thus, 100 µl of goat anti-human IgG (manufactured by TAG) diluted to 1 µg/ml in 0.1 M bicarbonate buffer, pH 9.6, is added to a 96-well plate (manufactured by Nunc), and is incubated overnight at 4° C. to immobilize the antibody. After blocking, 100 µl each of appropriately diluted antibody of the present invention or a sample containing the antibody, or 100 µl of human IgG (manufactured by CAPPEL) as the standard is added, and incubated at room temperature for 1 hour.

After washing, 100 µl of 5000-fold diluted alkaline phosphatase-labeled anti-human IgG antibody (manufactured by BIO SOURCE) is added, and incubated at room temperature for 1 hour. After washing, the substrate solution is added and incubated, followed by the measurement of absorbance at 405 nm using the MICROPLATE READER Model 3550 (manufactured by Bio-Rad) to calculate the concentration of the desired antibody.

The altered IL-6 for use in the present invention has an activity of binding to IL-6 receptor and does not transmit the biological activity of IL-6. Thus, the altered IL-6, though it competes with IL-6 for binding to IL-6 receptor, does not transmit the biological activity of IL-6 and, thereby, it blocks signal transduction by IL-6.

Altered IL-6 may be constructed through the introduction of mutation by replacing amino acid residues of the amino acid sequence of IL-6. IL-6, the source of the altered IL-6, may be of any origin, but when the antigenicity is to be considered, it is preferably human IL-6.

Specifically, the secondary structure of IL-6 is predicted using a known molecular modeling program of the amino acid sequence, for example WHATIF (Vriend et al., J. Mol. Graphics (1990), 8, 52-56), and the overall effects on the amino acid residue to be replaced is evaluated. After an appropriate amino acid residue has been determined, mutation is introduced to effect amino acid substitution by the commonly used polymerase chain reaction (PCR) method using a vector containing the base sequence encoding human IL-6 gene as a template thereby to obtain a gene encoding an altered IL-6. This is then integrated, as desired, into an appropriate expression vector, from which the altered IL-6 can be obtained according to the expression, production and purification methods of said recombinant antibody.

Specific examples of the altered IL-6 are disclosed in Brakenhoff et al., J. Biol. Chem. (1994) 269, 86-93, and Savino et al., EMBO J. (1994) 13, 1357-1367, WO 96-18648, and WO 96-17869.

The IL-6 partial peptide or the IL-6 receptor partial peptide for use in the present invention has an activity of binding to IL-6 receptor or IL-6, respectively, and does not transmit the biological activity of IL-6. Thus, the IL-6 partial peptide or the IL-6 receptor partial peptide specifically inhibits the binding of IL-6 to IL-6 receptor by binding to IL-6 receptor or IL-6, respectively, and thereby capturing it. As a result, they do not transmit the biological activity of IL-6, and thus block signal transduction of IL-6.

The IL-6 partial peptide or the IL-6 receptor partial peptide is a peptide comprising some or all of the amino acid sequence of the region involved in the binding to IL-6 and IL-6 receptor in the amino acid sequence of IL-6 or IL-6 receptor. Such a peptide generally comprises 10-80, preferably 20-50, more preferably 20-40 amino acid residues.

The IL-6 partial peptide or the IL-6 receptor partial peptide can be constructed by specifying the region involved in the binding to IL-6 and IL-6 receptor in the amino acid sequence of IL-6 or IL-6 receptor, and by producing some or all of the amino acid sequence by a conventional method such as a genetic engineering technology or a peptide synthesis method.

In order to prepare the IL-6 partial peptide or the IL-6 receptor partial peptide by a genetic engineering technology, the DNA sequence encoding the desired peptide is integrated into an expression vector, from which the peptide can be obtained by the expression, production, and purification methods of said recombinant antibody.

Preparation of the IL-6 partial peptide or the IL-6 receptor partial peptide by the peptide synthesis method can be effected using a method commonly used in peptide synthesis such as the solid phase synthesis or the liquid phase synthesis.

Specifically the method described in Zoku-Iyakuhin no Kaihatsu (Sequel to Development of Pharmaceuticals), Vol. 14, Peputido Gousei (Peptide Synthesis), edited by Haruaki Yajima, Hirokawa Shoten, 1991, may be used. The solid phase synthesis method used includes, for example, a reaction in which an amino acid corresponding to the C-terminal of the peptide to be synthesized is coupled to a support which is insoluble in organic solvents, and then an amino acid in which α-amino group or a side chain functional group has been protected with an appropriate protecting group is condensed one amino acid at a time from the C-terminal to the N-terminal direction, and a reaction in which said protecting group of the α-amino group of the amino acid or the peptide coupled to the resin is eliminated are alternately repeated to elongate the peptide chain. The solid phase peptide synthesis methods are divided into the Boc method and the Fmoc method depending on the type of protecting group to be used.

After the synthesis of the desired peptide is complete, a deprotection reaction and a reaction for cleaving the peptide chain from the support are carried out. For cleavage from the peptide chain, hydrogen fluoride or trifuluoromethane sulfonic acid in the Boc method, and TFA in the Fmoc method are generally used. In the Boc method, for example, the above protected peptide resin is treated in hydrogen fluoride in the presence of anisole. Subsequently, the protecting group is eliminated and the peptide is recovered by cleaving from the support. By lyophilizing, the crude peptide can be obtained. On the other hand, in the Fmoc method, the deprotection reaction and the cleavage reaction of the peptide from the support may be performed in TFA for example, in a procedure similar to the above.

The crude peptide thus obtained can be applied to HPLC for its separation and purification. Its elution can be carried out in a water-acetonitrile solvent system that is commonly used for protein purification under an optimum condition. The fraction corresponding to the peak of the profile of the chromatography obtained is collected and lyophilized. The peptide fraction thus purified is identified by subjecting it to the analysis of molecular weight by mass spectroscopic analysis, the analysis of amino acid composition, or the analysis of amino acid sequence, and the like.

Specific examples of the IL-6 partial peptide or the IL-6 receptor partial peptide are disclosed in Japanese Unexamined Patent Publication (Kokai) 2-188600, Japanese Unexamined Patent Publication (Kokai) 7-324097, Japanese Unexamined Patent Publication (Kokai) 8-311098, and United States Patent Publication US 5210075.

The activity of the IL-6 antagonist for use in the present invention of blocking signal transduction of IL-6 can be evaluated using a conventionally known method. Specifically, the IL-6-dependent human myeloma cell line (S6B45, KPMM2), human Lennert's T-lymphoma cell line KT3, or IL-6-dependent cell MH60.BSF2 is cultured, to which IL-6 is added, and the activity can be evaluated using the incorporation of $^{3}$H-thymidine into the IL-6-dependent cell in the coexistence of the IL-6 antagonist.

Alternatively, U266, an IL-6 receptor-expressing cell, may be cultured, to which $^{125}$I-labeled IL-6 is added and an IL-6 antagonist is added at the same time, and then the $^{125}$I-labeled IL-6 bound to the IL-6 receptor-expressing cell is determined. In the above assay system, a negative control group containing no IL-6 antagonists, in addition to the group in which an IL-6 receptor antagonist is present, is set up, and the results obtained for them are compared to evaluate the IL-6-inhibiting activity of the IL-6 antagonist.

As described in the Example below, anti-IL-6 receptor antibody exhibited a therapeutic effect on inner ear disorders, suggesting that IL-6 antagonists such as anti-IL-6 receptor antibody are effective as a therapeutic agent for inner ear disorders.

The subject to be treated in the present invention is mammals. The subject mammal to be treated is preferably humans.

The preventive or therapeutic agents of the present invention may be administered, either orally or parenterally, systemically or locally. For example, intravenous injection such as drip infusion, intramuscular injection, intrapleural injection, intraperitoneal injection, subcutaneous injection, suppositories, intestinal lavage, oral enteric coated tablets, and the like can be selected, and the method of administration may be chosen, as appropriate, depending on the age and the condition of the patient. The effective dosage is chosen from the range of 0.01 mg to 100 mg per kg of body weight per administration. Alternatively, the dosage in the range of 1 to 1000 mg, preferably 5 to 50 mg per patient may be chosen.

Preferred dosages and preferred methods of administration are such that, in the case of anti-IL-6 receptor antibody, the amounts wherein free antibody is present in the blood are effective dosages. In specific examples, 0.5 mg to 40 mg per kg of body weight, preferably 1 mg to 20 mg, per month (4 weeks) are administered in one to several doses, for example in the administration schedule of twice per week, once per week, once every two weeks, once every four weeks and the like by intravenous injection such as drip infusion and subcutaneous injection. The administration schedule can be adjusted by observing the disease conditions and blood levels of laboratory tests by, for example, extending the administration interval from twice per week or once per week to once per two weeks, once per three weeks, once per four weeks, and the like.

The preventive and/or therapeutic agents for inner ear disorders of the present invention may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof depending on the dosage form.

EXAMPLES

The present invention will now be explained in more details with reference to the working examples and reference examples. It should be noted, however, that the present invention is not limited to them in any way.

Example 1

Experimental Procedure (1) Measurement of Hearing Ability of Mice before Acoustic Load For 4 week-old male C57BL/6J mice, hearing ability by the auditory brainstem response (ABR) was measured on the day before acoustic load. Before measurement, xyladine and ketamine were intraperitoneally injected to effect sufficiently deep anesthesia, and during measurement additional anesthesia with ketamine was conducted as needed.

(Auditory Brain-evoked Response) To know the magnification of noise induced hearing loss in this noise condition, we tested the threshold shift with auditory brainevoked response (ABR). ABR measurements were performed using waveform storing and stimulus control of Scope software of PowerLab system (model: PowerLab2/20, ADInstruments CastleHill, Australia), EEG recording with extraceluler amplifier Digital Bioamp system (model: BAL-1, Tucker-Davis Technologies FL/USA). Sound stimuli were produced by a coupler type speaker (model: ES1spc, BioResearch-Center Nagoya/Japan) inserted into the external auditory canal of mice. Tone burst stimuli, 0.1 ms rise/fall time (cosine gate) and 1 ms flat segment, were generated and the amplitude were specified by sound generator and attenation Real-Time Processor and Programable Attenater (model: RP2.1 and PA5, Tucker-Davis Technologies FL/USA). Sound level calibration were done using Sound Level Meter (model: LA-5111, Ono Sokki Yokohama/Japan). For recording, stainless steel needle electrodes were placed at the vertex and ventro-lateral to the left and right ears. Generally, ABR waveforms were recorded for 12.8 ms at a sampling rate of 40,000 Hz using 50-5000 Hz bandpass filter settings, waveforms from 256 stimuli at a frequency of 9 Hz were averaged. ABR waveforms were recorded in 5-dB SPL intervals down from a maximum amplitude until no waveform could be visualized. Frequencies of sounds given for the measurement of hearing ability threshold level were three types of 4 kHz, 12 kHz and 20 kHz, and the hearing ability threshold level of each was measured.

(2) Creation of Hearing Loss Model

In an acoustic load instrument (an instrument in which the masking noise of the RION Audiometry AA67N was used as the sonifier, and as the amplifier a SONY SRP-P150 and a FOSTEX D-1405 were used for amplification, and then loaded with a speaker having a diameter of about 12 cm in a closed space), mice were housed in a metal-mesh cage with a height of 3 cm that was allowed to stand directly, at a distance of 1 cm, under the speaker. The cage was radially compartmentalized by metal nets with similar properties, and four animals were simultaneously housed in separate chambers. Then, under the condition that had previously been set up to provide a sound pressure of 124±1 db in the acoustic load instrument (a plurality of measurements during the two hour loading by a CASELA CEL-231), the animals were subjected to a load of a very loud sound for two hours. The acoustic load used was 4 kHz SPL Octave band noise. Also, a thermometer was placed in the acoustic load instrument to determine the temperature before and after the acoustic load.

(3) Drug Administration

After the above (2), the animals were divided into two groups (A and B), and 2 mg/body of IgG and 2 mg/body of MR16-1 (the anti-IL-6R humanized antibody prepared in Reference Example 4) were immediately given to the rats of each group. The administration was set as a blind test, and the technicians were informed of the administration in each group until the end of measurement of hearing ability.

(4) Measurement of Hearing Ability Threshold Level

In a manner similar to the above (1), hearing ability was measured one week after acoustic load and drug administration. After confirming deep anesthesia, the mice after measurement were decapitated to extract the temporal bone, which was fixed and then stored for histological examination.

(5) Analysis of Results

The difference between the hearing ability obtained in the above (4) and the hearing ability before treatment obtained in the above (1) was taken for each individual, and the degree of reduction in the hearing ability threshold level (dB) was calculated. The mean degree of reduction in the hearing ability threshold level (dB) was calculated for each of the MR16-1-administration group and the control group for each frequency.

Results

For one animal that died at the time of anesthesia in the above (4), the hearing ability could not be measured, and thus it was excluded. The number of animals for which the degree of hearing ability threshold level was obtained was n=4 for the MR16-1-administration group, and n=2 for the IgG-administration group. The temperature in the acoustic load instrument was 25° C. before the load and 27° C. after the load. The results are shown in the following Table 1 and FIG. 1.

TABLE 1

| Frequency used | IgG-administration control group | MR16-1-administration group | Difference in changes in the threshold level |
|---|---|---|---|
| 4 kHz | 22.5 | 37.5 | −15 |
| 12 kHz | 35 | 27.5 | +7.5 |
| 20 kHz | 55 | 28.8 | +26.3 |

Discussion

Acoustic trauma is a physical external force that is called sound pressure, and thus the model used in this experiment is considered to be a physical tissue-damaged model of the cochlea. In this experiment, very loud sounds centering on a frequency of 4 kHz have been applied. In the cochlea, sensors that perceive sounds are spatially dispersed depending on the frequency (tonotropic), and thus the fact that the hearing ability reduction in the control group is significant at 4 kHz and it becomes smaller as it becomes away therefrom to the high frequency region may be accounted for by the fact that since the very loud sound was loaded at the 4 kHz region the tissue nearer to the region is more severely damaged.

On the other hand, in the IL-6 receptor antibody-administration group, at 12 kHz and 20 kHz, the reduction in hearing ability has been more suppressed as compared to the control group as it becomes further away from the site wherein the very loud sound was loaded and the tissue was directly damaged. The foregoing suggests that IL-6 receptor antibody has an effect of suppressing the special progression of hearing ability reduction in the tissue damage in the cochlea, i.e. sensorineural hearing loss in the inner ear disorders, or has an effect of suppressing the hearing ability reduction in the high frequency region in sensorineural hearing loss.

Example 2

The Expression of Inflammatory Cytokines in the Cochlea after Acoustic Trauma

Figure 2:
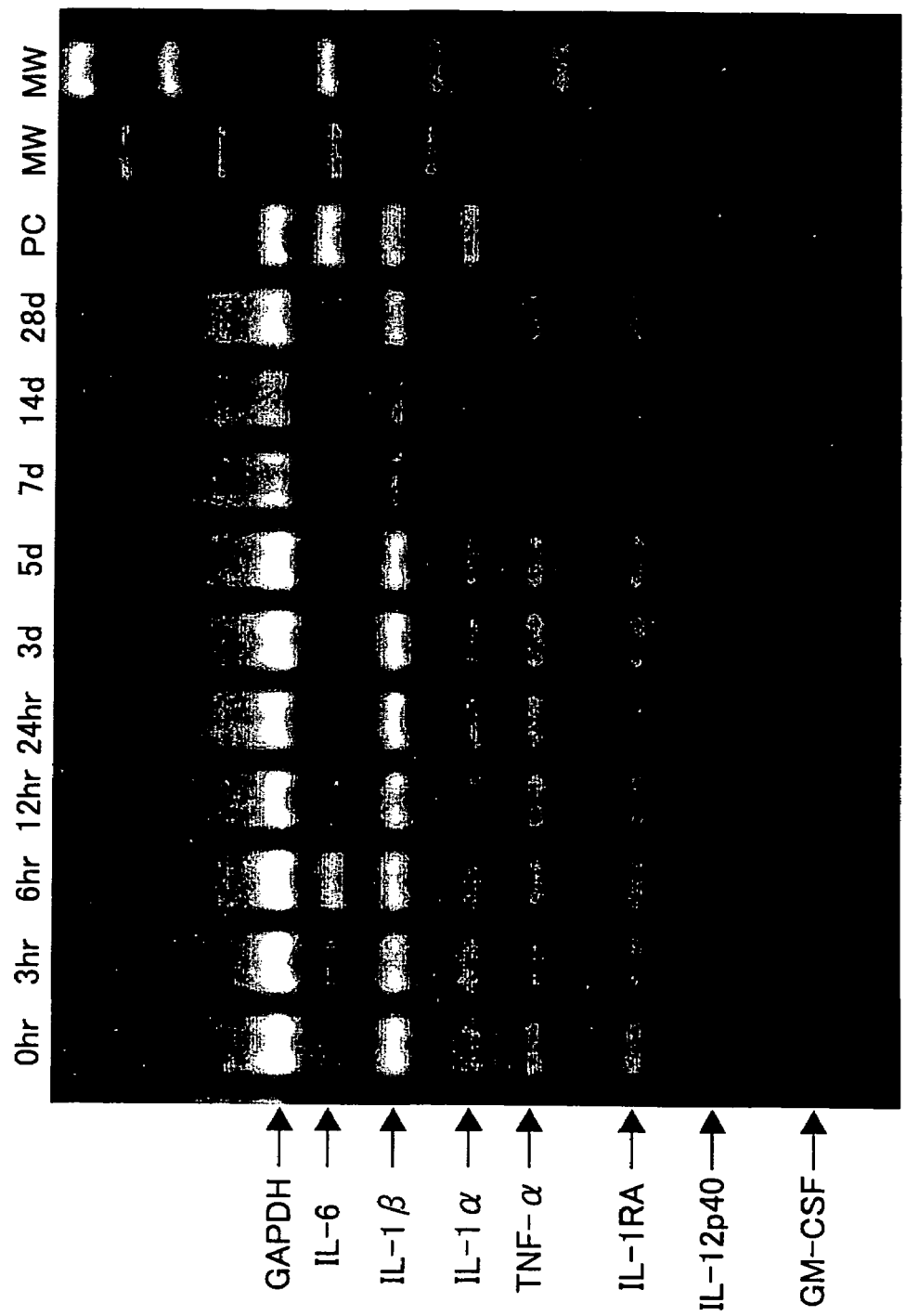
FIG. 2 is an electrophoretogram showing the result of RT-PCR in Example 2 indicating changes with time in various cytokines in the cochlea of SD rats after they were subjected to acoustic load.

A hearing loss model was created using 3-4 week-old male SD rats by a method similar to Example 1. At 3 hours, 6 hours, 12 hours, 24 hours, 3 days, 5 days, 7 days and 28 days after acoustic load, the temporal bone was extracted from each rat. While taking care to prevent the lymph in the cochlea from leaking, the cochlea was only extracted, and the expression of various inflammatory cytokines was determined by the RT-PCR method. The result is shown in FIG. 2. As can be seen from FIG. 2, in the cochlea of the acoustic trauma model, elevated expression was noted of TNF-α, IL-1α, IL-1β, IL-1 receptor antagonist (IL-1RA) and IL-6. On the other hand, no expression of IL-12p40 or GM-CSF was noted.

Figure 3:
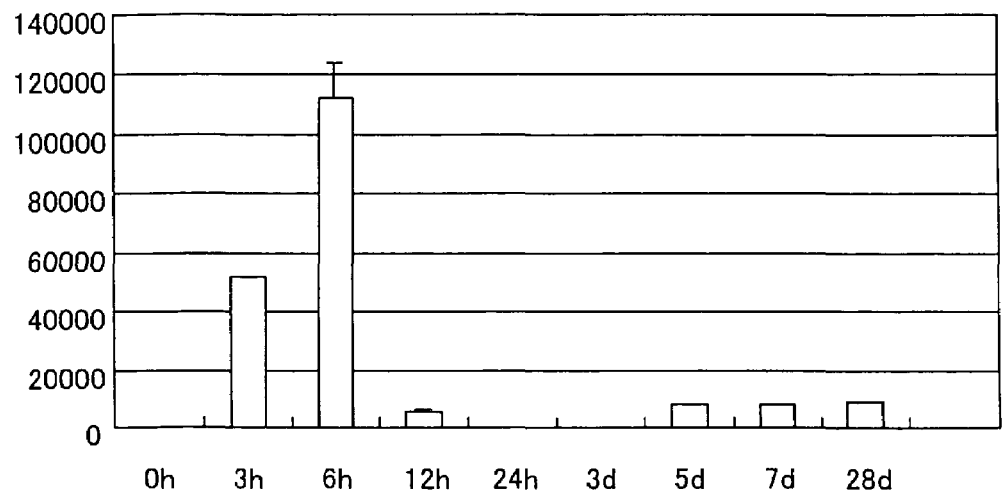
FIG. 3 is a graph showing the result of quantitative RT-PCR in Example 2 indicating changes with time in TNF-α in the cochlea of SD rats after they were subjected to acoustic load.
Figure 4:
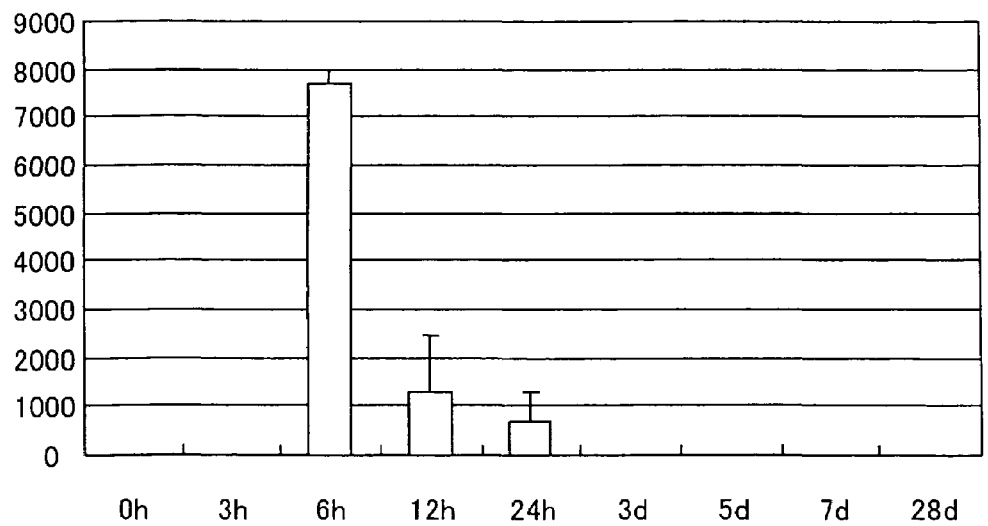
FIG. 4 is a graph showing the result of quantitative RT-PCR in Example 2 indicating changes with time in IL-6 in the cochlea of SD rats after they were subjected to acoustic load.
Figure 5:
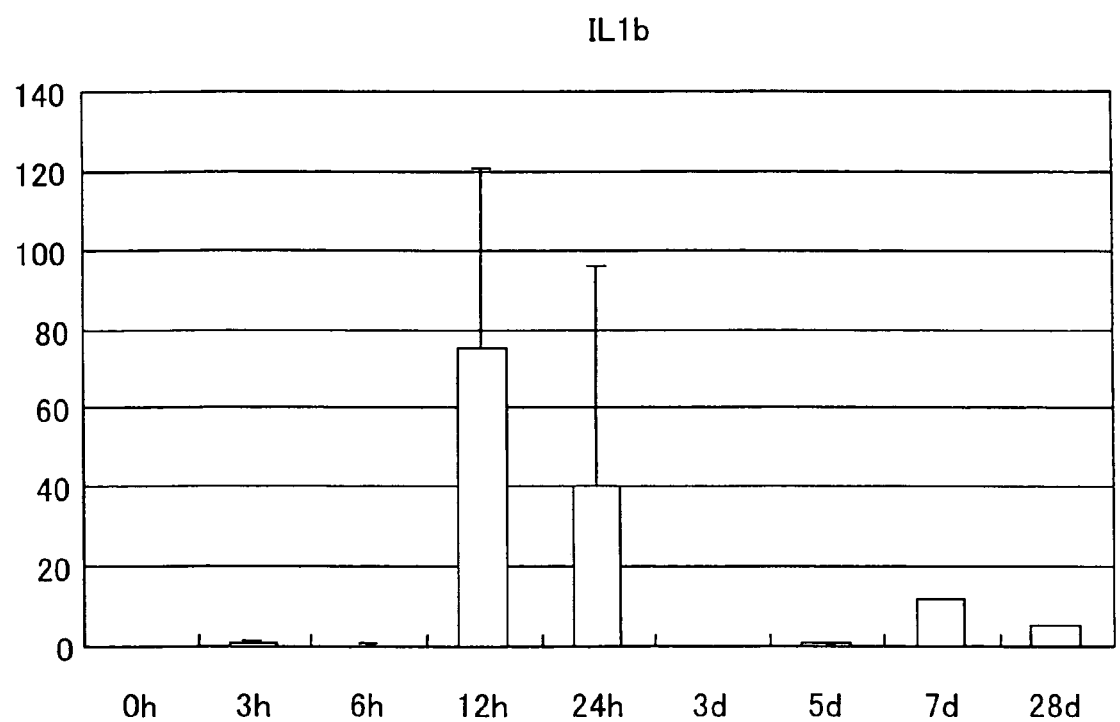
FIG. 5 is a graph showing the result of quantitative RT-PCR in Example 2 indicating changes with time in IL-1β in the cochlea of SD rats after they were subjected to acoustic load.

Then, changes in TNF-α, IL-6 and IL-1β with time were determined by a quantitative RT-PCR method. The quantitative RT-PCR method employed 18S rRNA as an internal control (reference gene) and analyzed the data by the ΔΔCt method. The results are shown in FIG. 3 to FIG. 5. As can be seen from FIG. 3 to FIG. 5, the expression of TNF-α, IL-1β and IL-6 was noted indicating the peak of the amount expressed in early stages within 24 hours after acoustic trauma.

Figure 7:
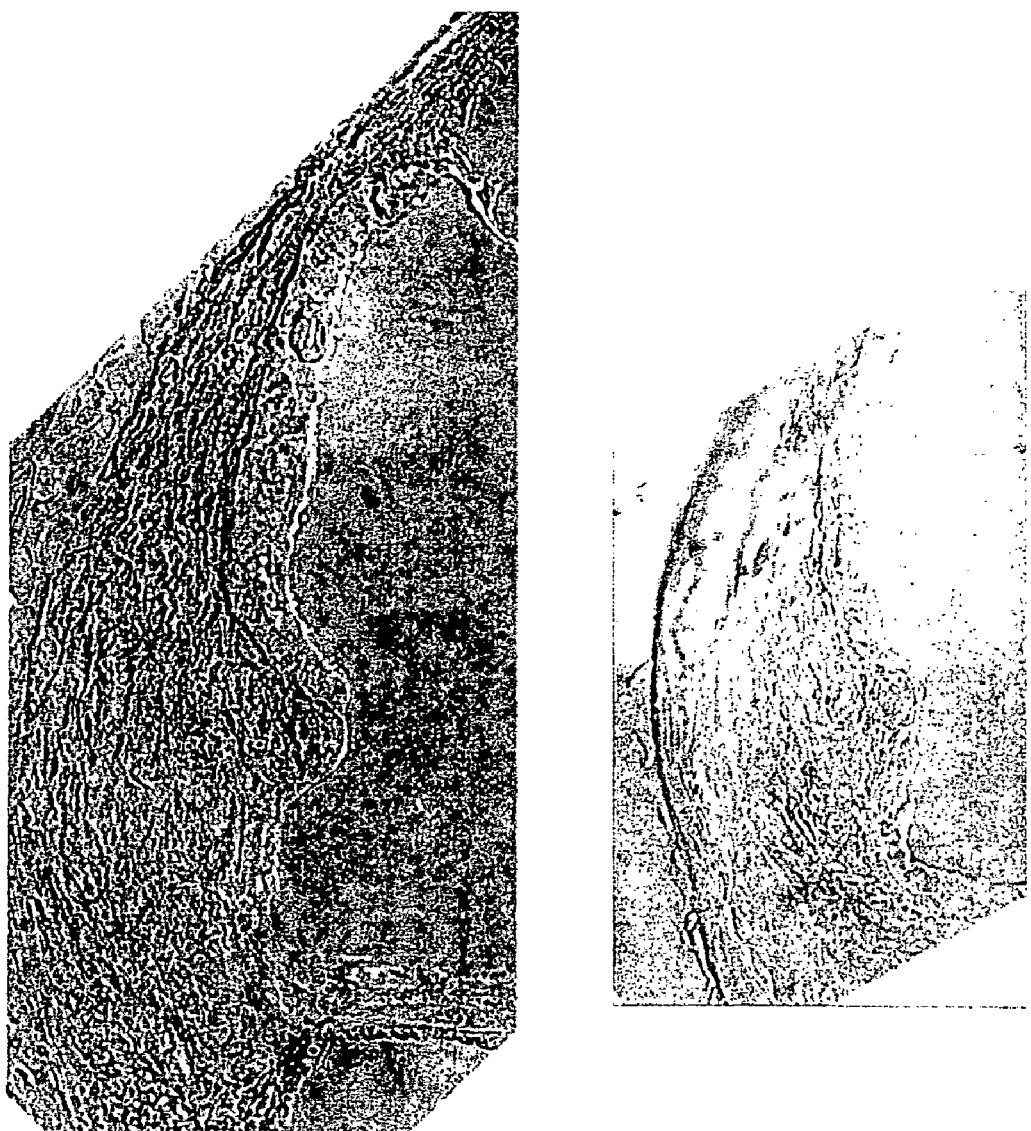
FIG. 7 is a photograph substituted for drawings showing the result in which IL-6 was detected with anti-mouse IL-6 antibody using Vectastein ABC kit in the tissue of SD rats six hours after they were subjected to acoustic load in Example 2.

Also, using the tissue at six hours after acoustic load, the lyophilized sections were immunohistologically stained. The animals used were SD rats, a hearing loss model was created as in Example 1, and the animals were decapitated six hours after the noise load. After extracting the temporal bone immediately, it was fixed in 4% paraformaldehyde for six hours, and demineralized with a 0.5 mol/l EDTA solution to obtain a sample, which was rapidly frozen in liquid nitrogen and sliced at a thickness of 7 μm using the cryostat (CM3000, Leica) to obtain a lyophilized section. The section was immunohistologically stained. The stain used the Vectastein ABC kit, and the DAB solution was used to develop color. As the stain control, a stain performed without adding the primary antibody was adopted. The results are shown in FIG. 6 to FIG. 7. As can be seen from FIG. 6 to FIG. 7, in the cochlea at six hours after acoustic load, the expression of IL-6 was noted in the basement membrane directly under the cochlear lateral wall and Corti's organ.

Example 3

Confirmation of Efficacy of Systemic Administration of an IL-6 Antagonist

Figure 8:
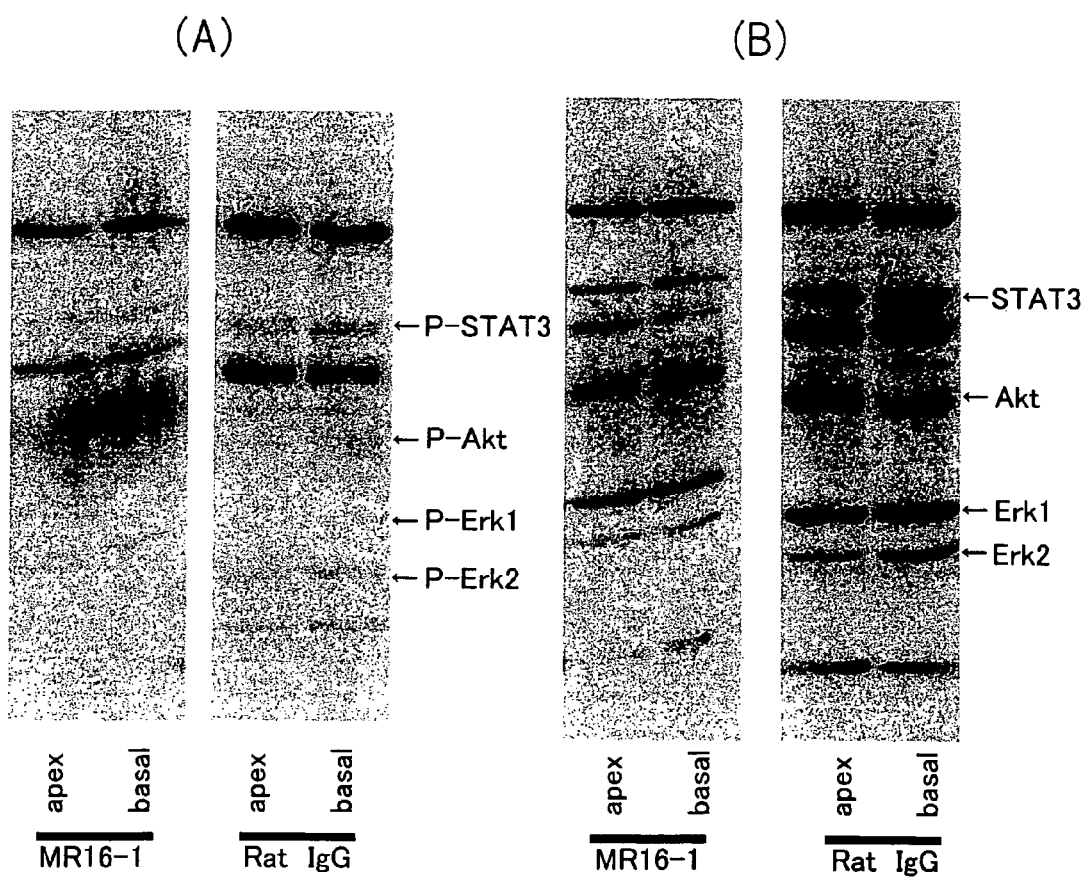
FIG. 8 is an electrophoretogram showing the result in which the expression of total STAT3, Erk and Akt, as well as phosphorylated STAT3, Erk and Akt was determined in the inner ear Corti's organ of C57BL/6J mice that received MR16-1 (the anti-IL-6R humanized antibody prepared in Reference Example 4) of the present invention or rat IgG (control) after they were subjected to a very loud sound of 124 dB for two hours.

In a manner similar to Example 1, male C57BL/6J mice were subjected to a load of a very loud sound of 124 dB for two hours, immediately followed by the intraperitoneal administration of MR16-1 at 2 mg/body and rat IgG at 2 mg/body. Eight hours after the administration of the antibody, the temporal bone was extracted and bilateral inner ears were extracted to dissect Corti's organ, which were divided into the first rotation (apex) and the second rotation (basal), and each of them was collected from both the left and the right, and combined. Using the Western blot method, the expression of total STAT3, Erk and Akt, and phosphorylated STAT3, Erk and Akt was determined. The result is shown in FIG. 8. As can be seen from FIG. 8, the signals of phosphorylated STAT3, phosphorylated Erk and phosphorylated Akt that were strongly noted in the control group were suppressed in the MR16-1-administration group. This result confirmed that the systemically administered MR16-1 exhibits efficacy in the cochlea.

This result and the result in Example 2 suggest that the effect by MR16-1 of suppressing IL-6 signals expressed in the cochlea soon after acoustic trauma contributes to the action mechanism of suppressing the hearing ability reduction by the intraperitoneal administration of MR16-1 shown in Example 1.

Reference Example 1

Preparation of Human Soluble IL-6 Receptor

Soluble IL-6 receptor was prepared by the PCR method using a plasmid pBSF2R.236 containing CDNA that encodes IL-6 receptor obtained according to the method of Yamasaki et al., (Yamasaki, K. et al., Science (1988) 241, 825-828). Plasmid pBSF2R.236 was digested with a restriction enzyme Sph I to obtain the cDNA of IL-6 receptor, which was then inserted into mp18 (manufactured by Amersham). Using a synthetic oligoprimer designed to introduce a stop codon into the cDNA of IL-6 receptor, a mutation was introduced into the cDNA of IL-6 receptor by the PCR method using the in vitro Mutagenesis System (manufactured by Amersham). The procedure resulted in the introduction of a stop codon to the amino acid at position 345, and gave cDNA encoding soluble IL-6 receptor.

In order to express the cDNA of soluble IL-6 receptor in CHO cells, it was ligated to a plasmid pSV (manufactured by Pharmacia) to obtain a plasmid pSVL344. The cDNA of soluble IL-6 receptor that was cleaved with Hind III-Sal I was inserted to plasmid pECEdhfr containing the cDNA of dhfr to obtain a plasmid pECEdhfr344 that can be expressed in the CHO cells.

Ten μg of plasmid pECEdhfr344 was transfected to a dhfr-CHO cell line DXB-11 (Urlaub G. et al., Proc. Natl. Acad. Sci. USA (1980) 77, 4216-4220) by the calcium phosphate precipitation method (Chen C. et al., Mol. Cell. Biol. (1987) 7, 2745-2751). The transfected CHO cells were cultured for 3 weeks in a nucleoside-free α MEM selection medium containing 1 mM glutamine, 10% dialyzed FCS, 100 U/ml penicillin, and 100 μg/ml streptomycin.

The selected CHO cells were screened by the limiting dilution method to obtain a single CHO cell clone. The CHO cell clone was amplified in 20 nM-200 nM methotrexate (MTX) to obtain a CHO cell line 5E27 that produces human soluble IL-6 receptor. The CHO cell line 5E27 was cultured in an Iscov-modified Dulbecco's medium (IMDM, manufactured by Gibco) containing 5% FBS. The culture supernatant was collected and the concentration of soluble IL-6 receptor in the culture supernatant was determined by ELISA. The result confirmed that soluble IL-6 receptor is present in the culture supernatant.

Reference Example 2

Preparation of Anti-human IL-6 Antibody

Ten μg of the recombinant IL-6 (Hirano et al., Immunol. Lett., (1988) 17, 41) was immunized to BALB/c mice together with Freund's complete adjuvant, and this was repeated every week until anti-IL-6 antibody could be detected in the serum. Immune cells were extracted from local lymph nodes and were then fused with a myeloma cell line P3U1 using polyethylene glycol 1500. Hybridomas were selected according to the method of Oi et al. (Selective Methods in Cellular Immunology, W.H. Freeman and Co., San Francisco, 351, 1980) that employs the HAT medium, and the hybridoma that produces anti-human IL-6 antibody was established.

The hybridoma that produces anti-human IL-6 antibody was subjected to the IL-6 binding assay as follows. Thus, a 96-well microtiter plate made of flexible polyvinyl (manufactured by Dynatech Laboratories, Inc., Alexandria, Va.) was coated with 100 μl of goat anti-mouse Ig (10 μl/ml, manufactured by Cooper Biomedical, Inc., Malvern, Pa.) overnight at 4° C. in 0.1 M carbonate-hydrogen carbonate buffer, pH 9.6. Subsequently, the plate was treated with 100 μl of PBS containing 1% bovine serum albumin (BSA) at room temperature for 2 hours.

After washing it in PBS, 100 μl of the hybridoma culture supernatant was added to each well, and then was incubated overnight at 4° C. The plate was washed, $^{125}$I-labeled recombinant IL-6 was added to each well to a concentration of 2000 cpm/0.5 ng/well, and then radioactivity of each well after washing was determined by a gamma counter (Beckman Gamma 9000, Beckman Instruments, Fullerton, Calif.). Of 216 hybridoma clones, 32 were positive in the IL-6 binding assay. From these clones, stable MH166.BSF2 was finally obtained. Anti-IL-6 antibody MH166 produced by said hybridoma has a subtype of IgG1κ.

Then, the IL-6-dependent mouse hybridoma clone MH60.BSF2 was used to examine a neutralizing activity with respect to the growth of the hybridoma by MH166 antibody. MH60.BSF2 cells were dispensed to $1\times10^4/200$ μl/well, and samples containing MH166 antibody were added thereto, cultured for 48 hours, 0.5 μCi/well of $^3$H-thymidine (New England Nuclear, Boston, Mass.) was added, and the culturing was continued for further 6 hours. The cells were placed on a glass filter paper and were treated by the automatic harvester (Labo Mash Science Co., Tokyo, Japan). As the control, rabbit anti-IL-6 antibody was used.

As a result, MH166 antibody inhibited, in a dose dependent manner, the incorporation of $^3$H-thymidine of MH60.BSF2 cells induced by IL-6. This revealed that MH166 antibody neutralizes the activity of IL-6.

Reference Example 3

Preparation of Anti-human IL-6 Receptor Antibody

Anti-IL-6 receptor antibody MT18 prepared by the method of Hirata et al. (Hirata, Y. et al. J. Immunol., (1989) 143, 2900-2906) was bound to CNBr-activated Sepharose 4B (manufactured by Pharmacia Fine Chemicals, Piscataway, N.J.) according to the attached regimen, and IL-6 receptor (Yamasaki, K. et al., Science (1988) 241, 825-828) was purified. A human myeloma cell line U266 was solubilized with 1 mM p-para-aminophenyl methane sulfonyl fluoride hydrochloride (manufactured by Wako Chemicals) (digitonin buffer) containing 1% digitonin (manufactured by Wako Chemicals), 10 mM triethanolamine (pH 7.8) and 0.15 M NaCl, and mixed with MT18 antibody bound to Sepharose 4B beads. Then, the beads were washed six times with the digitonin buffer to prepare the partially purified IL-6 receptor to be used for immunization.

BALB/c mice were immunized four times every ten days with the above partially purified IL-6 receptor obtained from $3\times10^9$ U266 cells, and then a hybridoma was prepared using a standard method. The hybridoma culture supernatant from the growth-positive well was tested for its activity of binding to IL-6 receptor according to the method described below. $5\times10^7$ U266 cells were labeled with $^{35}$S-methionine (2.5 mCi) and were solubilized with the above digitonin buffer. The solubilized U266 cells were mixed with a 0.04 ml volume of MT18 antibody bound to Sepharose 4B beads, and then were washed six times with the digitonin buffer. $^{35}$S-methionine-labeled IL-6 receptor was eluted with 0.25 ml of the digitonin buffer (pH 3.4) and was neutralized in 0.025 ml of 1M Tris (pH 7.4).

0.05 ml of the hybridoma culture supernatant was mixed with 0.01 ml of Protein G Sepharose (manufactured by Pharmacia). After washing, Sepharose was incubated with 0.005 ml $^{35}$S-labeled IL-6 receptor solution prepared as described above. The immunoprecipitate was analyzed by SDS-PAGE to investigate the hybridoma culture supernatant that reacts with IL-6 receptor. As a result, a reaction-positive hybridoma clone PM-1 (FERM BP-2998) was established. The antibody produced from the hybridoma PM-1 has a subtype of IgG1κ.

The inhibitory activity by the antibody produced by the hybridoma PM-1 on the binding of IL-6 to human IL-6 receptor was studied using the human myeloma cell line U266. A human recombinant IL-6 was prepared from *E. coli* (Hirano et al., Immunol. Lett., (1988) 17, 41-45), and was labeled with $^{125}$I using the Bolton-Hunter reagent (New England Nuclear, Boston, Mass.) (Taga, T. et al., J. Exp. Med. (1987) 166, 967-981).

$4 \times 10^5$ U266 cells were cultured with the culture supernatant of 70% (v/v) hybridoma PM-1 together with 14,000 cpm of $^{125}$I-labeled IL-6 for one hour. Seventy μl of the sample was layered on 300 μl FCS in a 400 μl microfuge polyethylene tube. After centrifugation, the radioactivity of the cell was determined.

The result revealed that the antibody produced by the hybridoma PM-1 inhibits the binding of IL-6 to IL-6 receptor.

Reference Example 4

Preparation of Mouse Anti-IL-6 Receptor Antibody

A monoclonal antibody directed against mouse IL-6 receptor was prepared according to the method described in Saito, et al., J. Immunol. (1991) 147, 168-173.

The CHO cells that produce mouse soluble IL-6 receptor were cultured in the IMDM culture liquid containing 10% FCS. From the culture supernatant, mouse soluble IL-6 receptor was purified using an affinity column in which anti-mouse IL-6 receptor antibody RS12 (see Saito, et al., supra) had been fixed to Affigel 10 gel (manufactured by Biorad).

The mouse soluble IL-6 receptor (50 μg) thus obtained was mixed with Freund's complete adjuvant, which was then injected to the abdomen of Wistar rats. From two weeks after the administration, the animals were boosted with Freund's incomplete adjuvant. On day 45, rat spleen cells were harvested, and about $2 \times 10^8$ cells thereof were fused with $1 \times 10^7$ mouse myeloma cells P3U1 using a 50% PEG1500 (manufactured by Boehringer Mannheim) according to the conventional method, and then were screened by the HAT culture medium.

After the hybridoma culture supernatant was added to the plate coated with rabbit anti-rat IgG antibody (manufactured by Cappel), mouse soluble IL-6 receptor reacted. Subsequently, using rabbit anti-mouse IL-6 receptor antibody and alkaline phosphatase-labeled sheep anti-rabbit IgG, hybridomas producing antibody directed against mouse soluble IL-6 receptor were screened by ELISA. Hybridoma clones for which antibody production was confirmed were subscreened twice to obtain a single hybridoma clone. The clone was designated as MR16-1.

The neutralizing activity of the antibody produced by the hybridoma on signal transduction of mouse IL-6 was examined by $^3$H-thymidine incorporation using MH60.BSF2 cells (Matsuda, T. et al., J. Immunol. (1988) 18, 951-956). To a 96-well plate, MH60.BSF2 cells were prepared at $1 \times 10^4$ cells/200 μl/well. To the plate were added 10 pg/ml mouse IL-6 and MR16-1 antibody or RS12 antibody at 12.3-1000 ng/ml, then were cultured at 37° C. and 5% $CO_2$ for 44 hours, and then 1 μCi/well of $^3$H-thymidine was added. After 4 hours, the incorporation of $^3$H-thymidine was measured. As a result, MR16-1 antibody suppressed the incorporation of $^3$H-thymidine by the MH60.BSF2 cells.

Thus, it was demonstrated that the antibody produced by the hybridoma MR16-1 (FERM BP-5875) inhibits the binding of IL-6 to IL-6 receptor.

The invention claimed is:

1. A method for treating sensorineural hearing loss or a vestibular disorder comprising administering to a subject in need thereof an antibody selected from the group consisting of a PM-1 antibody and an MR16-1 antibody;
   wherein said administration is effective for treating sensorineural hearing loss or a vestibular disorder in said subject.

2. The method according to claim 1 wherein said sensorineural hearing loss is sensorineural hearing loss caused by Meniere's disease, drug-induced inner ear disorders, viral inner ear disorders, purulent inner ear disorders, temporal bone fracture or acoustic nerve tumor.

3. The method according to claim 1 wherein said sensorineural hearing loss is sudden deafness, senile deafness or noise deafness.

4. The method according to claim 1 wherein said vestibular disorder is caused by Meniere's disease, vestibular neuronitis or is a drug-induced inner ear disorder.

5. The method according to claim 1 wherein said antibody is a recombinant antibody.

6. The method according to claim 1 wherein said antibody is a PM-1 antibody.

7. The method according to claim 1 wherein said antibody is an MR16-1 antibody.

8. The method according to claim 1 wherein said antibody is a chimeric antibody, a humanized antibody, or a human antibody.

9. The method according to claim 1 wherein said antibody is a humanized PM-1 antibody.

* * * * *